United States Patent [19]

McKay et al.

[11] Patent Number: 5,658,242
[45] Date of Patent: Aug. 19, 1997

[54] WALKING AID

[75] Inventors: Stewart Kenneth McKay; Christopher Kirtley, both of Molendinar, Australia

[73] Assignee: Polycane Australia Pty Ltd., Queensland, Australia

[21] Appl. No.: 350,746

[22] Filed: Dec. 7, 1994

(Under 37 CFR 1.47)

Related U.S. Application Data

[63] Continuation of Ser. No. 949,535, filed as PCT/AU92/00110, Mar. 13, 1992 published as WO92/16177, Oct. 1, 1992, abandoned.

[30] Foreign Application Priority Data

| Mar. 13, 1991 | [AU] | Australia | PK5065 |
| Aug. 30, 1991 | [AU] | Australia | PK8045 |

[51] Int. Cl.$^6$ ........................ A61H 3/00
[52] U.S. Cl. ................. 602/16; 602/23; 482/51
[58] Field of Search ............. 602/16, 19, 23, 602/24, 26, 5, 27; 482/51, 66; 403/53, 66, 327, 343; 601/33–35

[56] References Cited

U.S. PATENT DOCUMENTS

| 170,656 | 12/1875 | Allen | 602/19 |
| 691,050 | 1/1902 | Dronne | 403/327 |
| 2,010,482 | 8/1935 | Cobb | 602/16 X |
| 2,144,851 | 4/1939 | McCown | 446/377 |
| 2,593,187 | 4/1952 | Riechelson | 446/377 |
| 2,632,439 | 3/1953 | Hickerson | 602/16 |
| 2,690,176 | 9/1954 | Nelson | 602/16 |
| 2,705,491 | 4/1955 | Hickerson | 602/16 |
| 3,574,367 | 4/1971 | Jankowski | 403/343 X |
| 4,243,027 | 1/1981 | LaCourse | 602/23 |
| 4,422,453 | 12/1983 | Salort | 602/23 |
| 4,543,948 | 10/1985 | Phillips et al. | 602/24 X |
| 4,679,368 | 7/1987 | Pettinga et al. | 403/327 X |
| 4,872,665 | 10/1989 | Chareire . | |
| 4,901,710 | 2/1990 | Meyer | 602/24 |
| 4,926,845 | 5/1990 | Harris | 602/19 |

FOREIGN PATENT DOCUMENTS

| 85765 | 10/1921 | Australia | 602/23 |
| 2921227 | 12/1980 | Germany | 602/23 |
| 3013366A1 | 10/1981 | Germany . | |

OTHER PUBLICATIONS

International Search Report, dated 22 Jun., 1992 (Australian Patent Office—International Searching Authority).
Thompson, Samuel B., "An Anti–Scissoring Device for Patients with Cerebal Palsy"—Journal of Bone & Joint Surgery, p. 218; 1957.

*Primary Examiner*—Richard J. Apley
*Assistant Examiner*—Victor K. Hwang
*Attorney, Agent, or Firm*—Panitch Schwarze Jacobs & Nadel, P.C.

[57] ABSTRACT

A walking aid having a body support member (43, 70, 100) and a pair of leg support members (42, 90, 110, 112) each of which is interconnected by a central or crotch pivot (41, 79, 113) so as to be independently movable with respect to each other. In one embodiment the body support member is a back support member (43). In another embodiment the body support member is a waist belt or body strap (70, 100) and having one or more inguinal straps or connections straps (74, 104, 105) interconnecting the waist belt or body strap to the crotch pivot. Each leg support member (42, 90, 110, 112) may be attached to leg callipers, knee-ankle foot orthoses (KAFO'S) or other specialized leg supports or attachments.

12 Claims, 5 Drawing Sheets

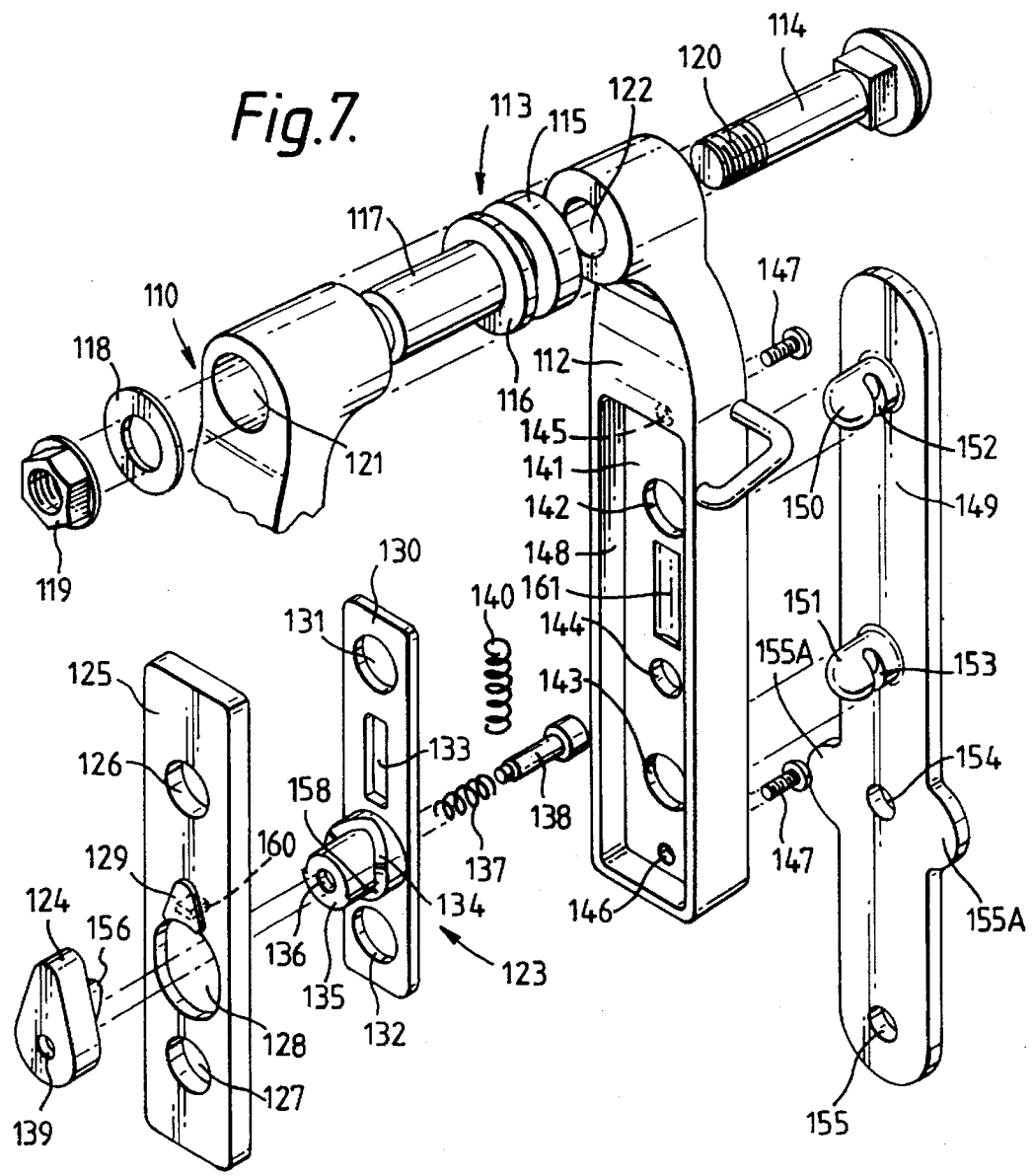

WALKING AID

This application is a continuation of application Ser. No. 07/949,535, which was filed as PCT/AU92/00110, Mar. 13, 1992 published as WO92/16177, Oct. 1, 1992, and which is now abandoned.

THIS INVENTION relates to a walking aid suitable for use with patients suffering from spinal complaints such as paraplegics and quadriplegics to walk or move.

Hitherto such walking aids have comprised a leg support apparatus, back support and chest support which were all interconnected by rigid straps usually formed from metal such as aluminium. The leg support apparatus as well as the back and chest support was normally formed from moulded plastics material. It was a characteristic of such conventional walking aids that the waist and chest support was pivotally attached to the leg support apparatus by a pair of pivot joints located in the hip region. By the provision of hip pivot joints or hinges it has now been ascertained that this placed considerable stress on the hip pivot joint when the patient swayed from side to side which is an essential part of the walking action. This means that a particular hip pivot joint supported substantially the entire weight of one leg which placed a severe bending movement on the hip pivot joint and especially on the bearing housing utilized an the pivot joint. This resulted in frequent breakage of the bearing housing and thus conventional walking aids as described above were subject to frequent maintenance, repair or replacement.

One conventional walking aid of the type referred to above was known as the PARAWALKER from the United Kingdom wherein the leg support apparatus included a foot support, knee support, and thigh support. Another conventional walking aid of the type described above was the LUISIANA from the United States wherein the leg support apparatus included a single foot and shin support as well as a thigh support.

Another conventional walking aid emanated from Germany and included a pair of leg members each having knee and thigh supports formed from leather straps interconnected by vertical metal arms. There was also included a flexible waist harness connected to a pair of upper thigh supports of each leg member. The upper thigh supports were spaced from each other by a spacer plate. There was also provided a pair of rods with each rod being attached to an adjacent lower leg member. Each rod was pivotally attached at an upper end thereof to the spacer plate. In this arrangement each leg member was therefore pivotally attached to the spacer plate for reciprocatable movement thereto simulating a walking action. However in this German walking aid there was no provision for a bearing between the spacer plate and each leg member which was necessary if the walking aid was useful for paraplegics or quadriplegics. The main reason for provision of the spacer plate was to keep the legs apart so that they did come into contact.

It is therefore an object of the invention to provide a walking aid which may alleviate the disadvantages of the prior art discussed above.

The walking aid of the invention includes a body support member and a pair of leg support members each of which are interconnected by a central or crotch pivot means so as to be independently pivotally movable with respect to each other.

The body support member may be of any suitable type and thus be rigid or flexible. Preferably in one embodiment the body support member includes a back support member. Suitably the back support member comprises a back frame having a plurality of frame members. In one preferred form the back support member may include a rear frame member extending away from the central pivot means. Suitably the rear frame member extends substantially horizontally or slightly upwardly with respect to the horizontal and then vertically upwardly so as to correspond to the contour of a patient's back. A chest bracket or frame member may be attached to an upper end of the frame member which may be curved or arcuate in plan. The chest bracket may have opposed ends interconnected by a chest belt or flexible strap.

However the above arrangement is not essential and thus the rear frame member may have cross members attached thereto for supporting the back of a patient at any suitable location. Alternatively the rear frame member may be bifurcated if desired.

The leg support members may be of any suitable type and may include leg support frames or leg support brackets which can support both the thigh and shin.

It is preferred however that the leg support member may simply comprise an attachment member which may be attached to an associated leg support such as a leg calliper such as those utilized in the aforementioned PARAWALKER or LUISIANA walking aids. Alternatively the attachment member may include a housing or casing being a suitable socket member for retaining a mating plug member or mounting projection of an associated leg support in either push fit or interference fit relationship. Alternatively clip means or other appropriate attachment means may be utilized if required, e.g. providing fasteners (e.g. screws or rivets) interconnecting mating parts of the attachment member and the leg calliper.

The pivot means suitably comprises a bearing housing and a pair of bearings which are independent of each other so as to enable an associated leg support member to be independently movable of the other. The bearings may be of any suitable type and thus include rolling element bearings such as ball bearings or roller bearings or plain bearings inclusive of bushings. Preferably ball bearings are utilized as they are a low friction bearing which will also withstand a reasonable amount of thrust.

The bearing housing may be tubular and suitably if the bearing is a ball bearing there is included an inner race or casing and an outer race or casing with balls interposed therebetween. The outer casing is suitably a very tight fit or interference fit within the tubular bearing housing.

The tubular bearing housing may be of any suitable shape but may have an arcuate or circular internal surface. An outer surface of the tubular bearing housing may have extending outwardly therefrom at least one stop and more preferably a plurality of stops to prevent the leg support members from contacting each other and thus facilitate unimpeded movement by the patient.

There also may be provided means for restricting rearward movement of each of the leg support members so as to enable a patient using the walking aid of the invention to achieve proper balance when in a standing position. Without such restricting means it may be necessary for the patient to use a walking stick or other support placed well to the rear to obtain a proper balance position or balance point. A suitable form of restricting means includes each leg support member also including one or more steps which engage with a rearwardly oriented stop of the tubular housing. However in another alternative such restricting means may comprise each leg support member having appropriately located abutment projections or stops contacting mating projections of the rear frame member at the balance point. In another possible arrangement the tubular bearing housing may have suitably located abutment members or stops which engage with respective edges of the leg support members at the balance point.

There also may be provided attachment means for attachment of each leg support member to the tubular bearing housing. This may include the use of fasteners such as nuts and bolts or clip means of a suitable type. Preferably the attachment means is also utilized to attach each bearing associated with an adjacent leg support member in the bearing housing.

In another embodiment of the invention the body support means may be modified to comprise a harness or more suitably a belt or corset worn by the patient around his waist and thus the back frame having a plurality of frame members may be dispensed with. In this regard it has been established that in some cases it may not be desirable to have any back support member in contact with the spine or coccyx and thus avoid any contact with relevant pressure points in these areas. With these points in mind the walking aid of the invention may include the central or crotch pivot means referred to above, a waist belt or corset which is attached to the pivot means and a pair of leg support members as discussed above.

In this embodiment of the invention the body support member may be used to support the pivot means in the desired position adjacent the crotch. The pair of leg members may each comprise a pair of attachment members which may each be attached to an associated leg support such as a calliper or specialized leg supports such as the knee-ankle foot orthoses (hereinafter "KAFO'S").

Suitably in this embodiment the crotch pivot means may include an axle which is attached to each of the leg attachment members. In this arrangement each leg attachment member may include a head part or upper part which may be hollow so that the axle may extend through aligned bores or internal passages located in each head part or upper part. Preferably in each bore or internal passage there is provided a plain bearing or bush suitably made of plastics material or ceramic material or even metal which may be moulded to the adjacent bore or internal passage or otherwise attached thereto. If necessary the bush or plain bearing may be dispensed with and replaced by a bearing surface of the internal passage or bore which may be suitably prepared or modified to allow rotatable movement by an associated leg attachment member.

The body support means may also include one or more connection members between the crotch pivot means and the belt. In one suitable arrangement the connection members may include connection straps which may be attached to the belt in any suitable manner such as by a fixed attachment which includes welding or stitching or being looped through a suitable attachment aperture or slot provided in the belt. This latter form of attachment may also be adjustable. Each connection strap may also be attached to the crotch pivot means.

In this embodiment the crotch pivot means may include a bearing support member to which each of the connection straps may be attached thereto in any suitable manner such as by stitching or welding for example. However it is preferred that the attachment between the bearing support member and each connection strap is adjustable and this may be achieved by each connection strap being looped through an associated aperture or slot in the bearing support member and with a free end of the connection strap being attached to the remainder of the strap by a VELCRO® fastener interconnection or buckle or other attachment of an adjustable nature.

If desired the adjustable attachment between each connection strap and the bearing support member may be replaced by a fixed attachment and instead there may be utilised an adjustable attachment between each connection strap and the support belt as described above. However the former arrangement is preferred.

The bearing support member may comprise a member having the shape of a substantially inverted U with the connection straps being attached to the base of the U and the axle being supported by internal bores or apertures in the arms of the U.

In another embodiment the inguinal straps may be modified so that they intersect or are crossed over so that one inguinal strap attached to a right side of the waist belt in use is attached to a left leg support member and an inguinal strap attached to a left side of the waist belt is attached to a right leg support member.

In regard to the above embodiment both of the leg support members may be provided with a support loop.

There also may be provided a releasable locking means whereby the wearer or user of the walking aid of the invention may attach both of the leg support members to the KAFO's. The locking means may be of any suitable type and preferably is a snap-on locking system which is readily releasable by actuation of a movable release member which may be moved linearly but is more preferably pivoted from a locked position to an unlocked position.

Reference may now be made to a preferred embodiment of the invention as shown in the attached drawings wherein:

FIGS. 1 and 2 illustrate the abovementioned prior art walking aids comprising the PARAWALKER and LUISIANA devices respectively;

FIG. 3 refers to a perspective view of a first type of walking aid constructed in accordance with the invention;

FIG. 4 refers to an exploded perspective view of the walking aid shown in FIG. 3;

FIG. 5 refers to a second type of walking aid constructed in accordance with the invention wherein the back support member is omitted.

FIG. 6 refers to a third type of walking aid constructed in accordance with the invention similar to that shown in FIG. 5;

FIG. 7 refers to an exploded perspective view of the walking aid shown in FIG. 6;

Figure 1:
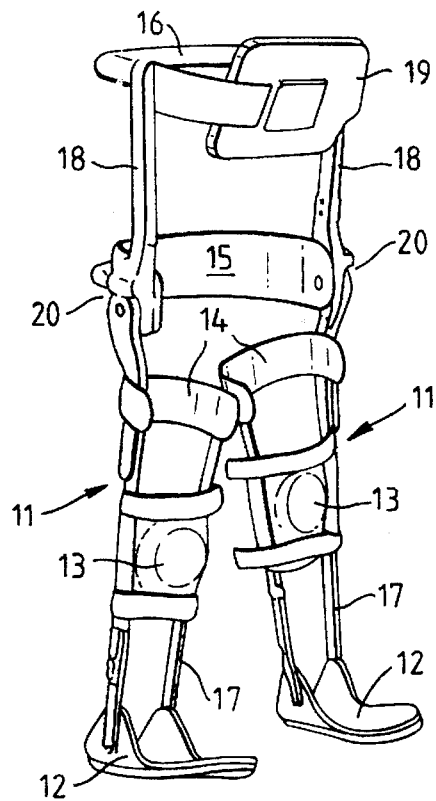

In the PARAWALKER device shown in FIG. 1 there is included leg callipers 11 including foot supports 12, knee supports 13 and rear leg supports 14. There is also shown back support 15 and chest support 16. Straps 17 interconnect foot supports 12 and knee supports 13. Straps 18 interconnect chest support 16 and back support 15. Chest support 16 also has chest pad 19. There is also shown hip joints 20.

Figure 2:
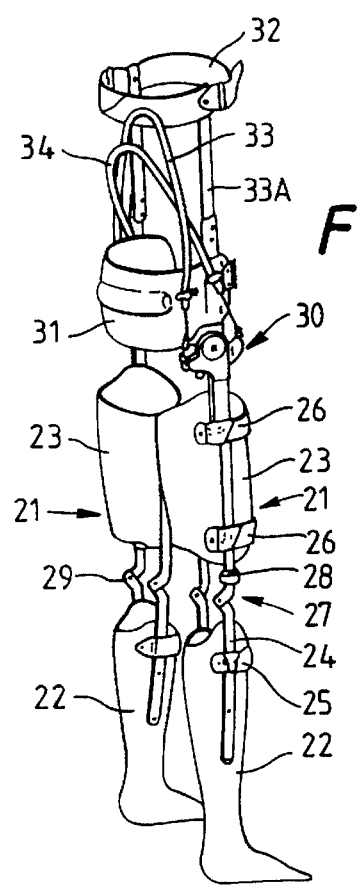

In the LUISIANA device shown in FIG. 2 there is included leg callipers 21 comprising foot supports 22 and upper leg supports 23 interconnected by straps 24 attached to foot supports 22 by attachment 25 and attached to upper leg supports 23 by attachments 26. There is also shown knee joints 27 comprising washer 28 and pivot joint 29 separate from each other and in the unlocked position. In the locked position washers 28 engage with pivot joints 29. Also shown are hip joints 30, back support 31, chest support 32 and straps 33A interconnecting chest support 32 and back support 31. Also shown are actuating cables 33 and 34 which work in conjunction with hip joints 30.

Figure 3:
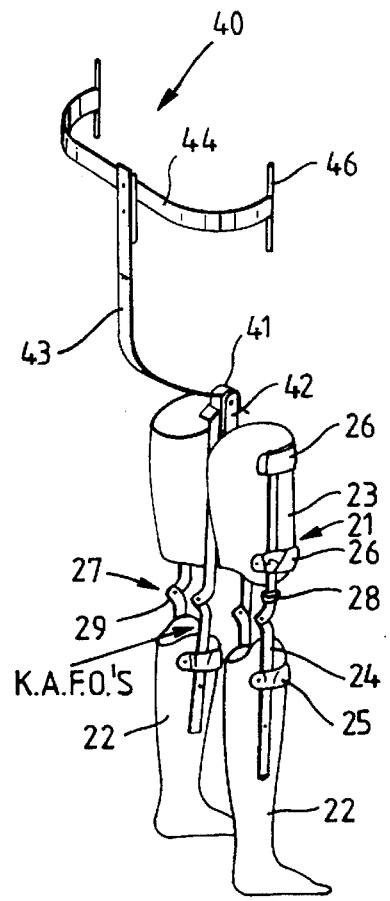

In FIG. 3 the walking aid 40 of the invention includes bearing housing 41, leg attachment members 42, back support member 43 in the form of a rear frame member and chest bracket 44 having associated therewith attachment members 46 for a chest belt (not shown). The leg attachment members are shown attached to leg callipers 21 already described in FIG. 2 above. However it will be appreciated that leg callipers 11 shown in FIG. 1 could also be attached to leg attachment members 42 if considered appropriate. Alternatively the leg callipers could be integral with the leg attachment members 42 so that the leg support members of the walking aid of the invention include within their scope the attachment members with the leg callipers omitted or the assembly of attachment members and leg callipers.

Figure 4:
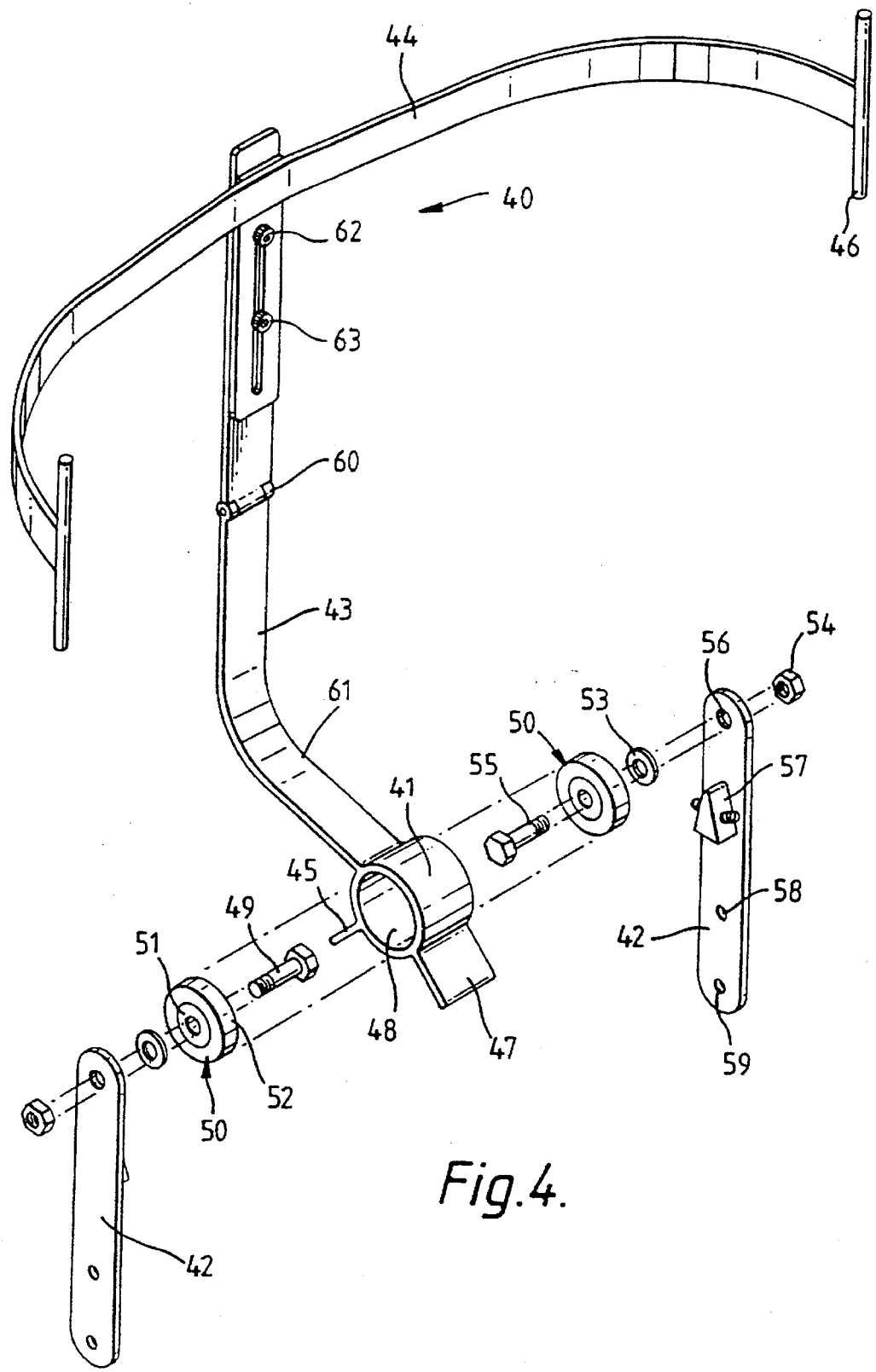

In FIG. 4 there is shown the walking aid 40 of the invention in greater detail. The tubular housing 41 has rear stop 45 and a front stop 47 which each extend the full width of housing 41 although it will be appreciated that this is not essential. Accommodated within the bore 48 of bearing housing 41 are bolts 49, bearings 50 having inner race 51 and outer race 52 and spacers 53. Bolts 49 are spaced from each other within bore 48 so as to provide a pair of bearings 50 which function independently of each other. There is also shown nuts 54 engageable with threaded ends 55 of bolts 49. The outer race 52 of each bearing 50 is a tight fit or interference fit within bore 48. Bolts 49 extend through aligned apertures 56 of attachment members 42 as shown.

Each attachment member 42 is provided with adjustable stops 57 which may engage with rear stop 45 of tubular housing 41 to achieve the balance point described previously. The leg calliper may be attached to a selected one of apertures 58 or 59. The back support member 43 may be formed from separate components if desired and jointed at locations 60 and 61 if appropriate. The position of the chest bracket 44 relative to back support member 43 may also be adjustable by the provision of fasteners 62 engageable in attachment slot 63.

Figure 5:
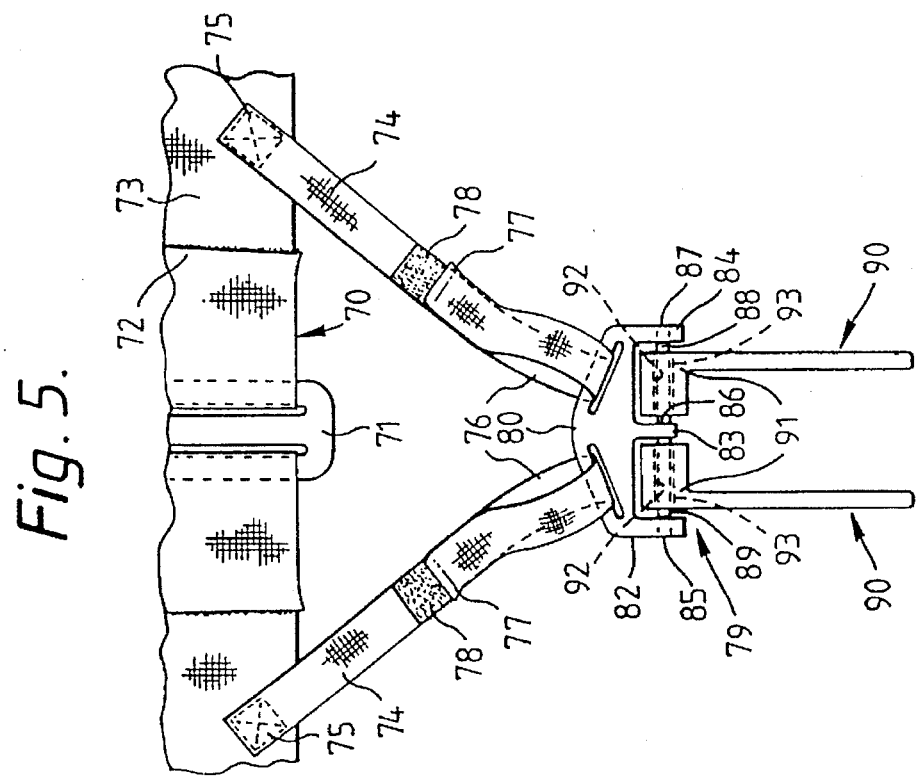

In FIG. 5 there is illustrated a body strap 70, which may be in the form of a belt or corset, adapted to be worn around the waist having a buckle 71 and VELCRO® fastener attachment parts 72 and 73 for adjustment. This may be replaced by a conventional buckle assembly if desired which includes a buckle tongue which engages with a selected hole in the belt. There is also shown connection or inguinal straps 74 attached to belt 70 at 75. Each connection belt 74 includes a loop 76 having a free end 77 attached to the remainder of strap 74 via a VELCRO® fastener attachment at 78. This provides an adjustable attachment as described above. This enables the straps 74 to be tensioned and thus stabilise the patient wearing the walking aid of the invention in a standing position.

There is also shown crotch pivot means 79 which includes bearing support member 80 which has downwardly depending projections 82, 83 and 84 which have aligned apertures 85, 86 and 87 for retention of axle 88. In one projection 82 there may be provided a blind hole which constitutes aperture 85 which retains an associated end 89 of axle 88. The axle 88 may be retained in desired position in projection 82, 83 and 84 by a grub screw (not shown) which extends through projection 83 or be provided with a threaded end (not shown) which engages with an internal thread located in projection 84 (not shown). Alternatively axle 88 may comprise two shafts each threaded in central projection 83.

Each leg member 90 is connected to the leg brackets (not shown) by bolts or snap fit or interference fit or alternative form of connection. Each leg member 90 also has an extended upper part 91 having an internal bore 92 which may be lined by a plain bearing or bush 93 which may be moulded in each bore 92 or attached thereto by an interference fit or other suitable connection.

Figure 6:
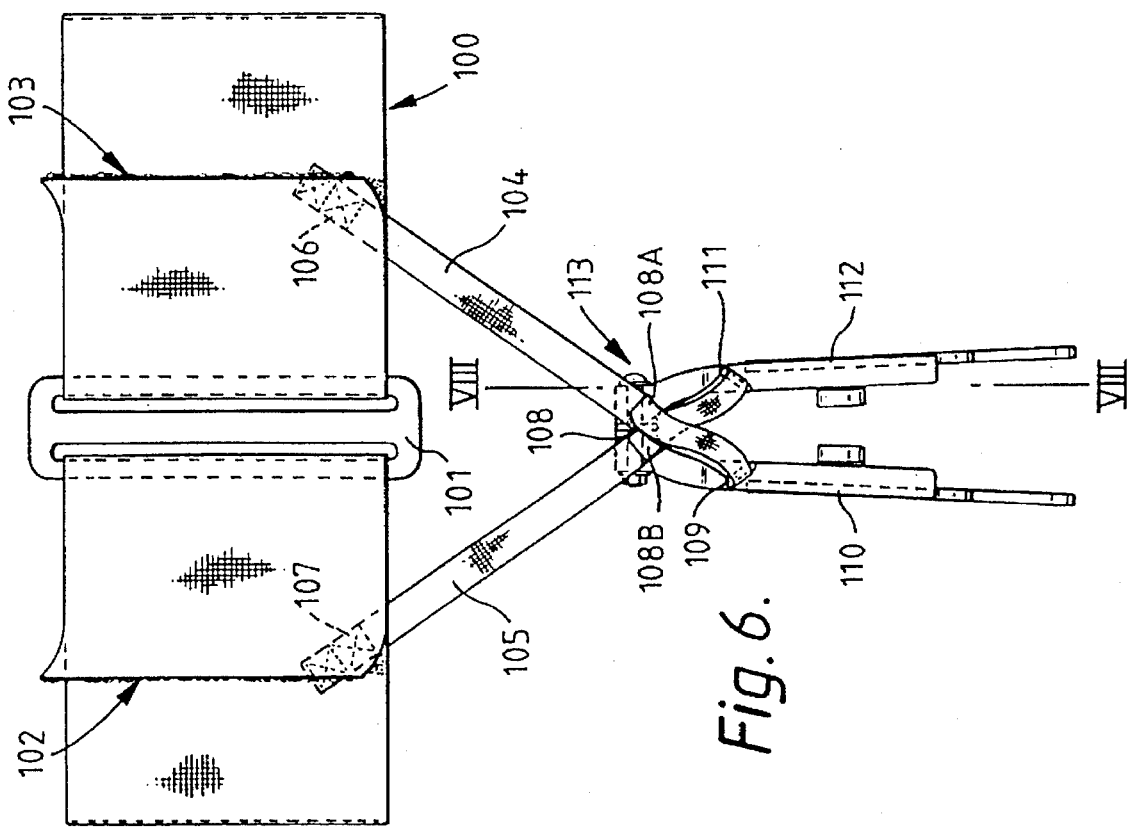

In FIG. 6 there is shown a modified walking aid of the invention when compared to the embodiment of FIG. 5. The waist belt or corset 100 has a buckle 101 and VELCRO® fastener attachment parts 102 and 103 for adjustment. The inguinal straps 104 and 105 are attached to waist belt 100 at 106 and 107 respectively by stitching or other form of attachment. The inguinal straps 104 and 105 are crossed or intersect at 108 so as to abut each other so that the right hand strap is looped through loop 109 attached to left leg support member 110 and the left hand strap 105 is looped through loop 111 attached to the right leg support member 112. The free end of each strap 104 and 105 may be attached to the strap by VELCRO® fastener or other suitable form of attachment at 108A and 108B.

The reason for the crossover is that by twisting the body (e.g. to the right) this puts tension on strap 104 which assists the left leg to be moved forward. In similar manner when the body is twisted to the left the right leg is assisted to move forward. The crossover is preferred because the natural swing of the body causes a twisting movement and this is utilised to assist in the rhythmic walking action.

It should be noted that the walking aid of the invention is based on a hip guidance orthosis or a pendulum effect and in some cases of lower level injuries the crossover may not be of assistance except possibly for walking up an incline or steps where a twist of the trunk would thrust the leg forward when the pendulum inertia is not present. However in the case of high level spinal injuries and particularly with a wide waist belt or corset swinging the upper body even as high as the shoulders particularly in the case of a quadriplegic the energy transmitted from the upper body in the wide belt through straps 104 and 105 to bearing 113 definitely assists in walking. The belt or corset 100 also gives the user excellent body support as in most cases people suffering from spinal injuries have lost muscle control in the stomach region.

Figure 8:
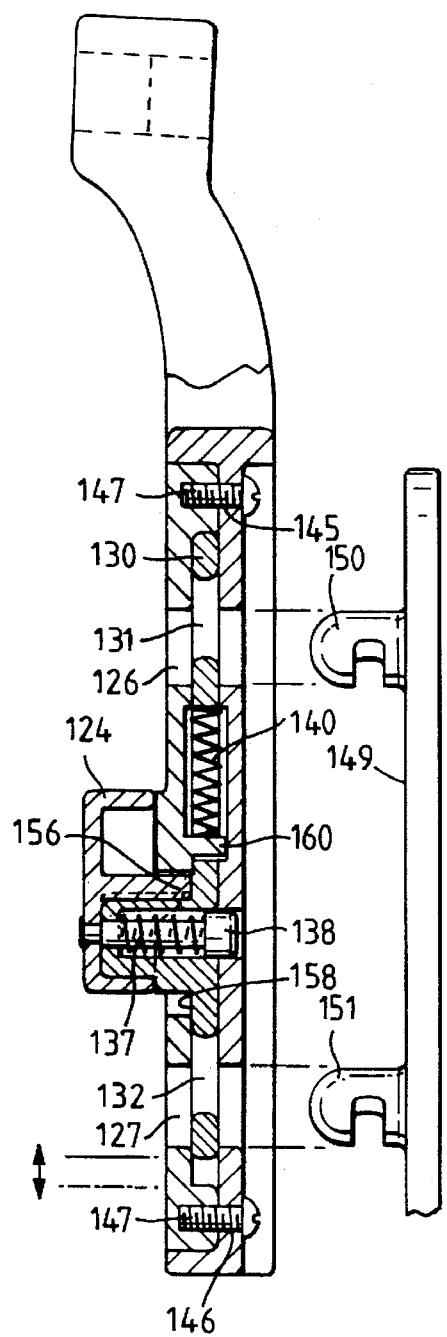
FIG. 8 is a sectional view of an assembled walking aid shown in FIG. 6, taken along lines VIII—VIII of FIG. 6.
Figure 9:
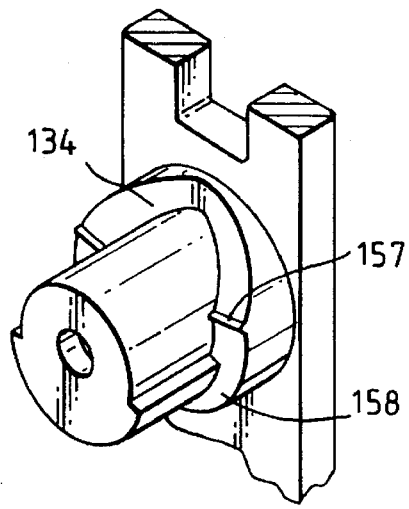
FIG. 9 is an enlarged view of the track for engagement with the cam trigger shown in FIGS. 7 and 8.
Figure 11:
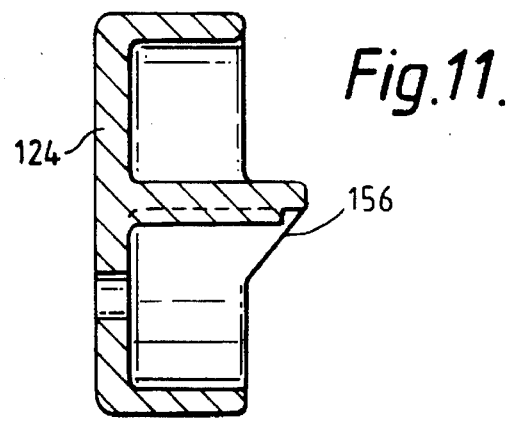
FIG. 11 is a sectional view of the cam trigger shown in FIG. 10, taken along lines XI—XI of FIG. 10.
Figure 10:
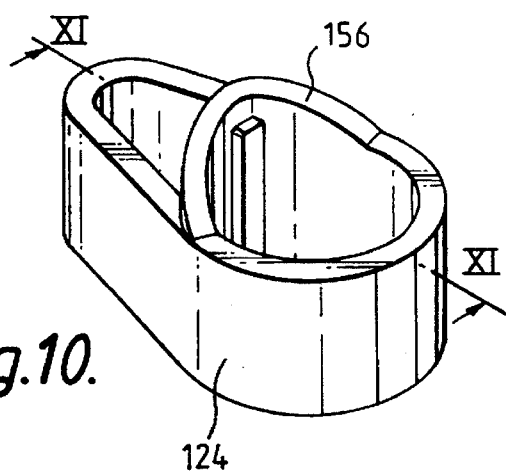
FIG. 10 is a perspective view of the cam trigger.

FIGS. 7–8 show a detailed view of a modified bearing means 113 for use in the invention through which leg support members 110 and 112 are pivotably attached thereto. The bearing means 113 includes axle bolt 114, spacer 115, bush 116, bearing 117, washer 118 and locknut 119 which is screw threadedly engaged to bolt 114 at 120. The bush 116 may take the role of a thrust bearing. Each leg support member 110 and 112 includes bores 121 and 122 for retention of bearing 113 and axle bolt 114. It will be appreciated that a number of different spacers 115 could be used so as to adjust the distance between support members 110 and 112. This will enable various users to be fitted with the walking aid of the invention as some paraplegics have varying levels of thigh muscle wasting.

FIGS. 7–10 also illustrate a releasable locking assembly 123 to the KAFO'S to be readily removed and attached to the leg support members 110, 112.

A KAFO is bolted or otherwise attached to an attachment member 149 through apertures 154, 155, and attachment member 149 are releasably lockable to its leg support member 112 by the locking assembly.

It will be appreciated that the location of the attachment apertures 154 and 155 may be variable not only widthwise having regard to enlarged parts 155A but also lengthwise in relation to attachment member 149 as may be required. This enables the bearing 113 to be moved in accordance with the posture of the user.

Releasable locking assembly 123 may include a cam trigger or release member 124, a cover member 125 having apertures 126 and 127, as well as central aperture 128 and upper shallow projection 129. Aperture 128 accommodates trigger 124 and projection 129 abuts trigger 124.

The locking assembly essentially works on a slide principle whereby a slide member 130 can slide within recess 141, bordered by a surround flange 148, between a lower unlocking position and an upper locking position.

Slide member 130 has two apertures 131 and 132 which align with apertures 142, 143 when the slide member 130 is in the lower unlocking position, and which are partially out of alignment (as illustrated in FIG. 8) when the slide member 130 is in its upper locking position.

Slide member 130 is naturally biassed into its upper locking position (as illustrated in FIG. 8) by a coiled spring 140, which sits within slot 133. The top of spring 140 abuts against the top wall of slot 133 while the bottom of spring 140 sits on top of projection 160 which is part of cover member 125. The leg support member 112 has a recess 161, as does the inner surface of cover member 125 in which spring 140 can locate to prevent the spring from rubbing against the walls of cover member 125 and leg support member 112.

The attachment member 149 has a pair of longitudinally spaced studs 150, 151, each stud having a slot therein 152, 153. Slots 152, 153 are of a size to allow the wall defining apertures 131, 132 to pass into the slot.

Thus, when slide member 130 is pushed downwardly into its unlocking position, apertures 131 and 142, and apertures 132 and 143 align and studs 150, 151 can be freely inserted into or removed from the aligned apertures.

However, when slide member 130 is moved to its upper locking position as illustrated in FIG. 8, the wall defining the apertures 131, 132 inserts into slots 152, 153 to lock the attachment member 149 to leg support member 112. As stated above, spring 140 naturally biasses slide member 130 into its locking position to prevent inadvertent release of the attachment member.

To lock the slide member 130 against downward movement, a cam trigger 124 and a sprung retaining screw 138 are provided. The retaining screw 138 can move longitudinally between a retracted position and an extended position, the latter position being illustrated in FIG. 8.

In the extended position, the head of screw 138 passes into aperture 144 and in the retracted position, the screw is pulled out from aperture 144. Extension of the screw into aperture 144 prevents the slide member 130 from moving downwardly thus locking it in the locked position. Pulling the screw 138 out from aperture 144 allows the slide member to slide downwardly into its unlocking position.

Retaining screw 138 extends through aperture 136 in shaft 135 and into aperture 139 of cam trigger 124, whereby it is attached to the cam trigger.

Screw 138 is biassed by spring 137 into its extended position but can be pulled into its retracted position by cam trigger 124 as the screw is securely held by the cam trigger. Rotation of cam trigger in a clockwise or anti-clockwise direction will cause projection 156 to ride along the cam track 134 on a shaft 135. This action causes the cam trigger to be raised in relation to shaft 135 which in turn causes the screw 138 to be pulled against the bias of spring 137 into its retracted position.

At this stage the cam trigger 124 can be pushed downwardly along elongate slot 128 which causes slide 130 to be pushed downwardly into its unlocking position.

As the cam trigger 124 is attached to screw 138, there is the tendency for spring 137 to force trigger 124 to ride down cam track 134 back to the initial position. To prevent this, a plateau portion 158 (see FIG. 9) is provided on shaft 135. When the projection 156 on cam trigger 124 is on the plateau portion 158, it will not be forced back to its initial position by spring 137. A rib 157 is provided which projection 156 must initially be pushed over to reach plateau portion 158. The projection prevents an inadvertent knock on cam trigger 124 from causing the trigger returning to its initial position.

To make studs 150, 151 robust, the studs are of an appreciable size. Thus apertures 126, 127 are provided in cover member 125 to accomodate the heads of the studs 150, 151. If apertures 126, 127 were not provided, the studs would need to be relatively short and thus would make them weaker. Screws 147 are provided to securely attach cover member 125 to leg support member 112. The screws pass through apertures 145, 146 and into threaded recesses (not shown) on cover member 125.

It would be appreciated from the foregoing that the walking aid of the invention provides substantial advantages over the prior art as discussed previously. These advantages are as follows:

1. The bearing housing may be located in the crotch area of the user which therefore is of great comfort to the user and not visually obvious especially when wearing clothes. Thus the walking aid of the invention is not obvious to an observer as it can be worn under the clothing.
2. The walking aid of the invention if formed from light weight plastics material would be extremely light in practice and would weigh a lot less than the prior art devices previously described. For example the walking aid of the invention would weigh approximately 4 kg when compared to a PARAWALKER device which would weigh approximately 10 kg.
3. The walking aid of the invention is extremely simple and efficient in use and does not have the complexity of the prior art devices. This makes it cheaper to manufacture.
4. It is possible for the walking aid of the invention to be manufactured using a series of interfitting modules or standard components. In this regard the user, while in a sitting position, may simply attach each of the leg callipers to the leg support members or leg attachment members.
5. The provision of a central pivot joint in the crotch area results not only in concealing of the bearings but also reduces the stresses which are present in the prior art devices. This reduces costs insofar as maintenance, repair or replacement is concerned. As mentioned above the prior art devices were subject to damage if the whole weight of one leg was concentrated on one hip joint.
6. The walking aid of the invention may be made entirely from plastics material which makes it suitable for production by injection moulding, compression moulding or other form of plastics moulding process. This is not the case with the prior art.
7. The combination of the waist belt, inguinal or connection straps, crotch pivot or bearing and leg support members provides a cohesive walking aid for patients suffering from spinal injury and has the advantages described above.

We claim:

1. A leg brace assembly comprising a crotch coupling assembly to pivotally couple a pair of leg braces together in a person's crotch area, each leg brace having an inner leg portion and an outer leg portion, the inner leg portion being connected to the crotch coupling assembly to allow the leg braces to pivot only about a horizontal axis and unable to twist relative to each other, the crotch coupling assembly being the only pivotal coupling to either of the leg braces.

2. The leg brace assembly of claim 1, wherein the crotch coupling assembly has sides which can pivot relative to each other, and the leg braces are rigidly connected to the respective sides of the crotch coupling assembly.

3. The leg brace assembly of claim 2, including body support means extending from the crotch coupling assembly.

4. The leg brace assembly of claim 3, wherein the body support means includes a belt or corset attachable to the body of the person.

5. A crotch coupling assembly to pivotally couple a pair of leg braces together in a person's crotch area, the assembly having a pair of elongate leg brace support members, each member adapted to extend along an inside leg portion of the person and from the crotch area towards the knee; pivot means to pivotally connect the members relative to each other only about a horizontal axis, the pivot means being above each member such that each member depends from the pivot means and the pivot means being adapted to be positioned within the crotch area, the members being unable to twist towards and away from each other; each member having means to allow a leg brace to be attached to the member adjacent the inside leg portion of the person, the assembly providing the only pivotal coupling to either of the leg braces.

6. The assembly of claim 5, wherein the leg brace support members are rigid in construction and are pivotally connected to each other by a common pivot pin.

7. The assembly of claim 6, wherein the leg support brace members are adapted to be releasably attachable to the leg braces.

8. The assembly of claim 7, wherein each leg brace support member has an outer wall which is adapted to face and be closely spaced from the person's inner leg area, and an inner wall which is adapted to face towards the person's other leg, and the means to allow a leg brace to be attached to the member includes a portion on the outer wall.

9. The assembly of claim 8, wherein the means to allow a leg brace to be attached to the member further includes a releasable locking assembly which includes a knob on the inner wall which is operable by the person to release the leg brace from the respective leg brace support member.

10. The assembly of claim 9, wherein the locking assembly is located within a housing on the respective leg brace support member.

11. The assembly of claim 5, further including body support means extending from the crotch coupling assembly.

12. The assembly of claim 11, wherein the body support means includes at least one belt or corset which can be attached to the body of the person.

* * * * *